(12) United States Patent
Fuller et al.

(10) Patent No.: US 11,490,895 B2
(45) Date of Patent: Nov. 8, 2022

(54) GUIDE EXTENSION CATHETER WITH EXPANDABLE BALLOON

(71) Applicant: BOSTON SCIENTIFIC SCIMED, INC., Maple Grove, MN (US)

(72) Inventors: Jeffrey Steven Fuller, Brooklyn Park, MN (US); Rachel Japuntich, Roseville, MN (US); Louis Warner Stefanich, Minneapolis, MN (US); James M. Anderson, Corcoran, MN (US); Benjamin Philip Gundale, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 647 days.

(21) Appl. No.: 15/448,545

(22) Filed: Mar. 2, 2017

(65) Prior Publication Data
US 2017/0252043 A1    Sep. 7, 2017

Related U.S. Application Data

(60) Provisional application No. 62/303,213, filed on Mar. 3, 2016.

(51) Int. Cl.
*A61B 17/12*    (2006.01)
*A61M 25/10*    (2013.01)
(Continued)

(52) U.S. Cl.
CPC ............... *A61B 17/12031* (2013.01); *A61B 17/12109* (2013.01); *A61B 17/12136* (2013.01);
(Continued)

(58) Field of Classification Search
CPC .............. A61M 25/01; A61M 25/04; A61M 25/0662; A61B 17/12031;
(Continued)

(56) References Cited

U.S. PATENT DOCUMENTS 4,564,014 A    1/1986    Fogarty et al.
4,616,652 A    10/1986   Simpson
(Continued)

FOREIGN PATENT DOCUMENTS

DE    3621350 A1    1/1988
DE    3819372 C1    1/1990
(Continued)

OTHER PUBLICATIONS

International Search Report and Written Opinion dated May 31, 2017 from International Application No. PCT/US2017/020545.
(Continued)

*Primary Examiner* — Nathan R Price
*Assistant Examiner* — Justin L Zamory
(74) *Attorney, Agent, or Firm* — Seager, Tufte & Wickhem LLP

(57) ABSTRACT

Medical devices and methods for making and using medical devices are disclosed. An example medical device may include a guide extension catheter. The guide extension catheter may include a proximal shaft having a first outer diameter. A distal sheath may be attached to the proximal shaft and may have a second outer diameter greater than the first outer diameter. The distal sheath may be designed to extend past a coronary ostium and into a coronary artery so that another medical device can pass therethrough toward the coronary artery. An expandable balloon may be coupled to the distal sheath.

7 Claims, 17 Drawing Sheets

(51) Int. Cl.
*A61M 25/01* (2006.01)
*A61M 25/04* (2006.01)
*A61M 25/06* (2006.01)
*A61M 25/00* (2006.01)
A61M 25/09 (2006.01)
A61B 17/00 (2006.01)
A61B 90/00 (2016.01)

(52) U.S. Cl.
CPC ........ *A61M 25/0069* (2013.01); *A61M 25/01* (2013.01); *A61M 25/04* (2013.01); *A61M 25/0662* (2013.01); *A61M 25/10* (2013.01); A61B 2017/00477 (2013.01); A61B 2017/00876 (2013.01); A61B 2017/1205 (2013.01); A61B 2090/3966 (2016.02); A61M 25/0052 (2013.01); A61M 2025/0018 (2013.01); A61M 2025/09125 (2013.01); A61M 2025/1052 (2013.01); A61M 2210/125 (2013.01)

(58) Field of Classification Search
CPC ........ A61B 17/12109; A61B 17/12136; A61B 2017/00876; A61B 2017/00477; A61B 2017/1205; A61B 17/3439; A61F 2/0013
See application file for complete search history.

(56) References Cited

U.S. PATENT DOCUMENTS

| | | |
|---|---|---|
| 4,762,129 A | 8/1988 | Bonzel |
| 5,120,323 A | 6/1992 | Shockey et al. |
| 5,232,445 A | 8/1993 | Bonzel |
| 5,267,982 A | 12/1993 | Sylvanowicz |
| 5,299,575 A * | 4/1994 | Sandridge ....... A61M 25/09041 600/435 |
| 5,385,562 A | 1/1995 | Adams et al. |
| 5,441,489 A | 8/1995 | Utsumi et al. |
| 5,484,412 A * | 1/1996 | Pierpont ............. A61M 25/104 604/101.03 |
| 5,527,292 A | 6/1996 | Adams et al. |
| 6,066,126 A | 5/2000 | Li et al. |
| 6,231,543 B1 * | 5/2001 | Hegde ................... A61M 25/10 606/192 |
| 6,537,294 B1 | 3/2003 | Boyle et al. |
| 6,575,958 B1 | 6/2003 | Happ et al. |
| 6,638,268 B2 | 10/2003 | Niazi |
| 6,695,793 B2 | 2/2004 | Brennan et al. |
| 6,953,454 B2 | 10/2005 | Peterson et al. |
| 7,294,124 B2 | 11/2007 | Eidenschink |
| 7,316,678 B2 | 1/2008 | Nash et al. |
| 7,717,899 B2 | 5/2010 | Bowe et al. |
| 7,762,984 B2 | 7/2010 | Kumoyama et al. |
| 3,048,032 A1 | 11/2011 | Root et al. |
| 8,142,413 B2 | 3/2012 | Root et al. |
| 8,292,850 B2 | 10/2012 | Root et al. |
| 2002/0165574 A1 * | 11/2002 | Ressemann ...... A61B 17/12045 606/194 |
| 2003/0100849 A1 | 5/2003 | Jang |
| 2004/0059179 A1 | 3/2004 | Maguire et al. |
| 2004/0116832 A1 | 6/2004 | Friedrich et al. |
| 2006/0030876 A1 | 2/2006 | Peacock, III et al. |
| 2009/0177120 A1 | 7/2009 | Tockman et al. |
| 2009/0264865 A1 | 10/2009 | Kawai |
| 2010/0030186 A1 | 2/2010 | Stivland |
| 2010/0217237 A1 | 8/2010 | Itou et al. |
| 2010/0234876 A1 | 9/2010 | Watson |
| 2014/0012281 A1 | 1/2014 | Wang et al. |

FOREIGN PATENT DOCUMENTS

| | | |
|---|---|---|
| EP | 0277366 A1 | 8/1988 |
| EP | 0704226 A1 | 4/1996 |
| EP | 1479409 A1 | 11/2004 |
| EP | 1639951 A1 | 3/2006 |
| WO | 03049798 A2 | 6/2003 |

OTHER PUBLICATIONS

Fuller, Jeffrey Steven, et al., U.S. Appl. No. 62/169,541, filed Jun. 1, 2015, entitled "Guide Extension Catheter".

* cited by examiner

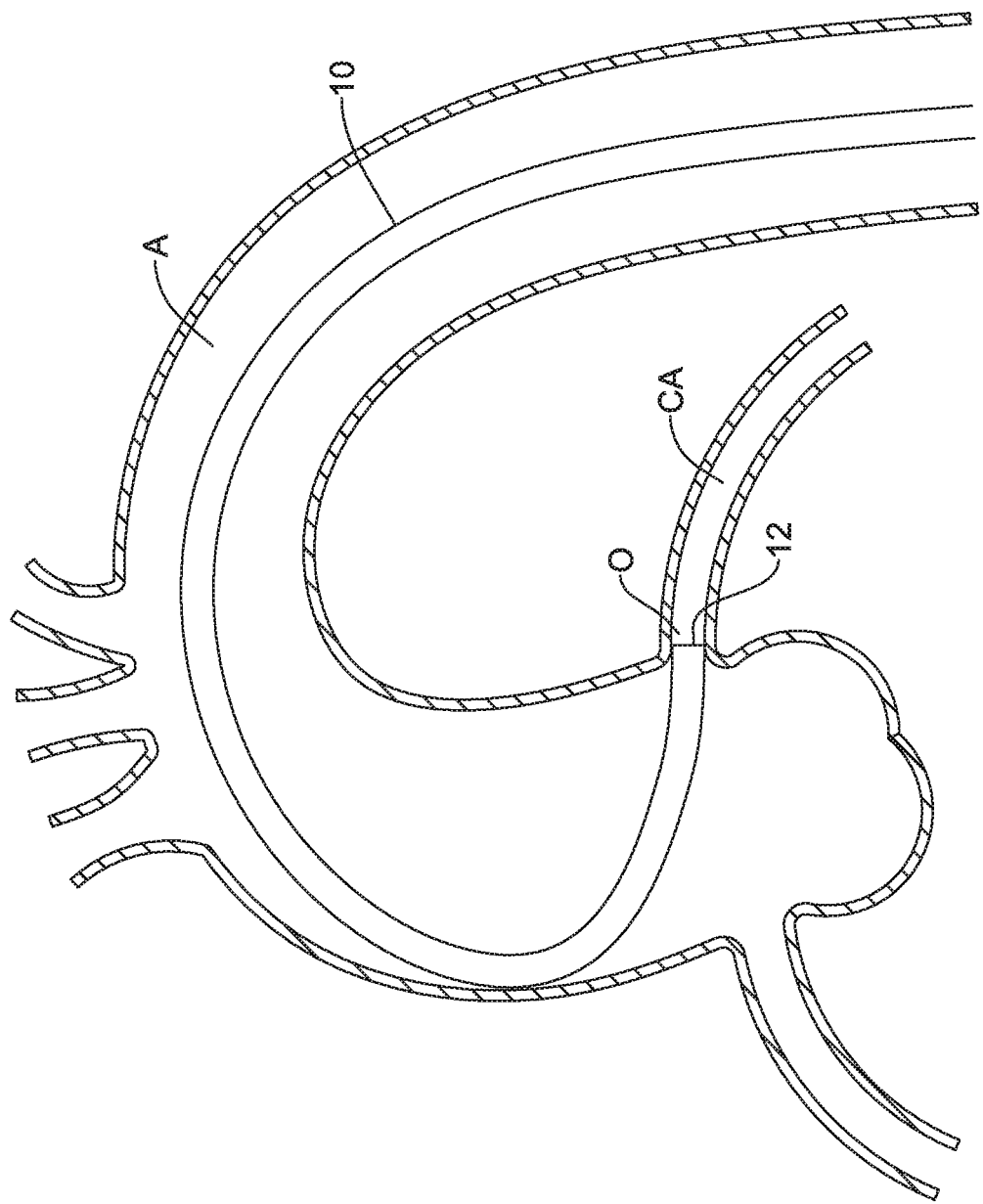

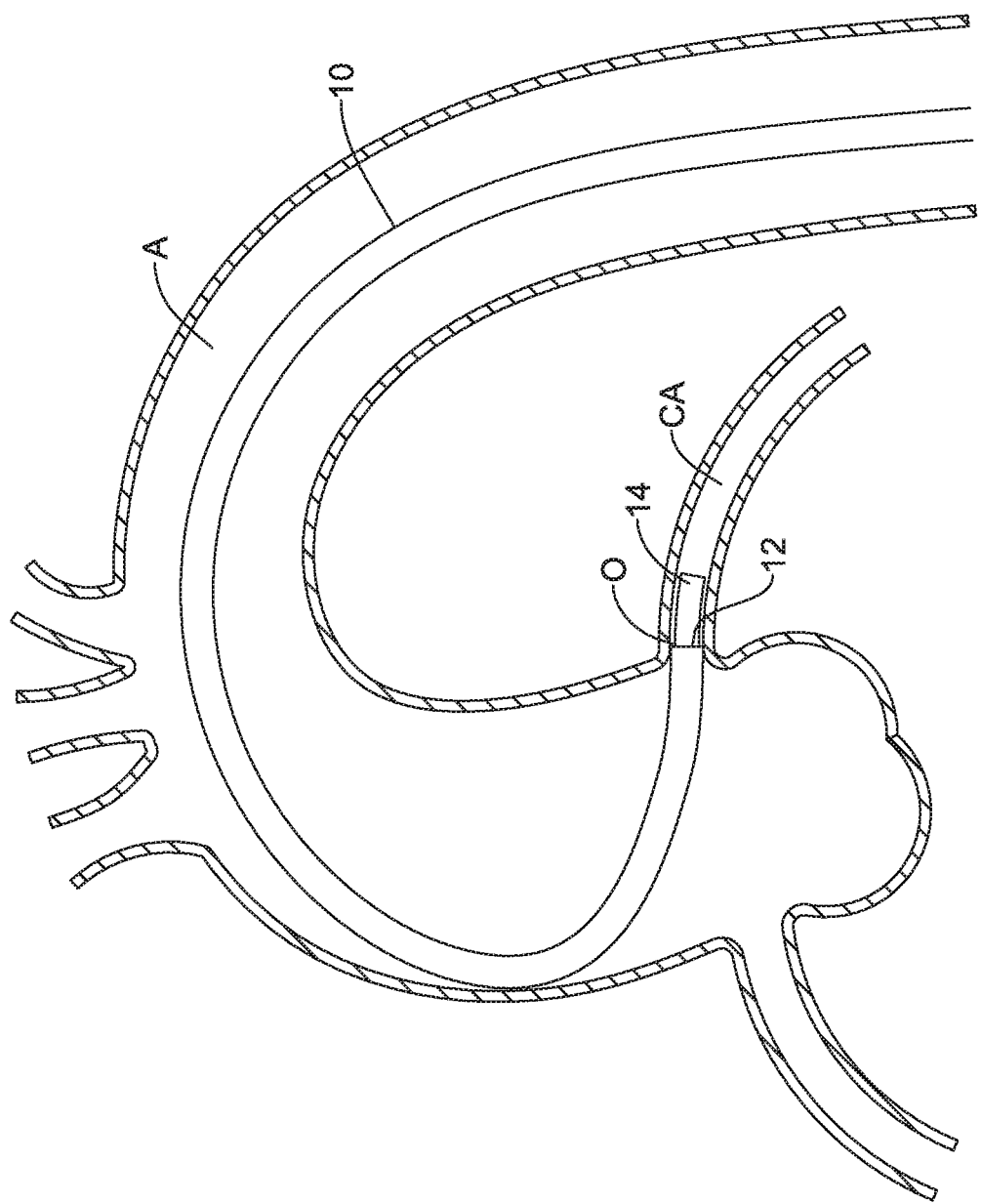

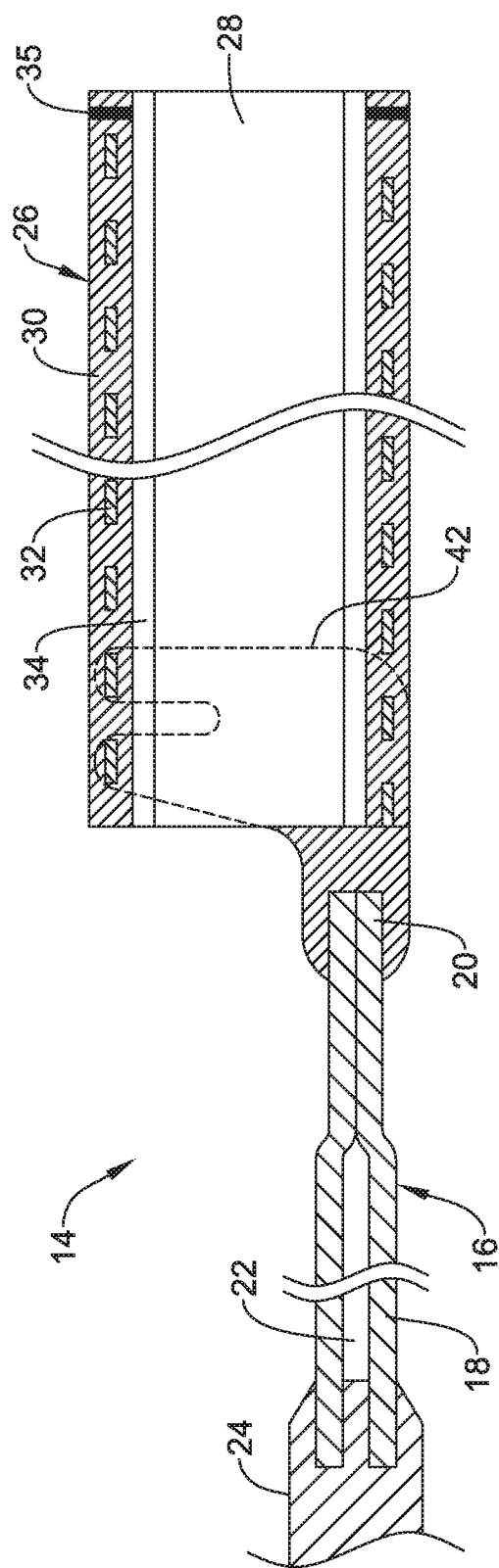

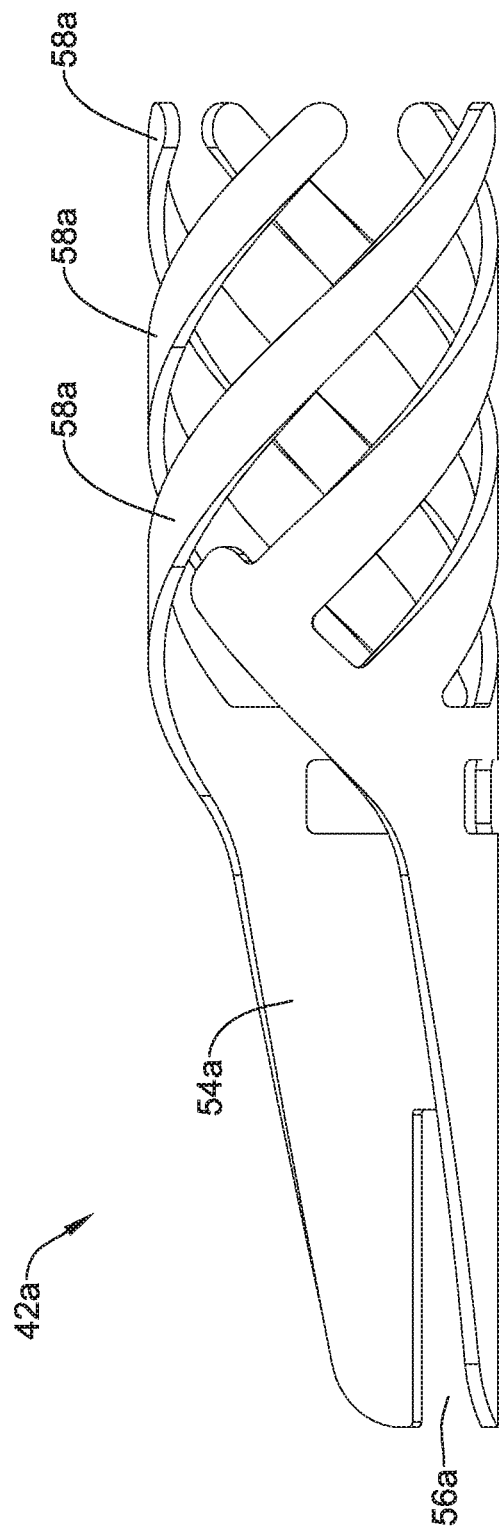

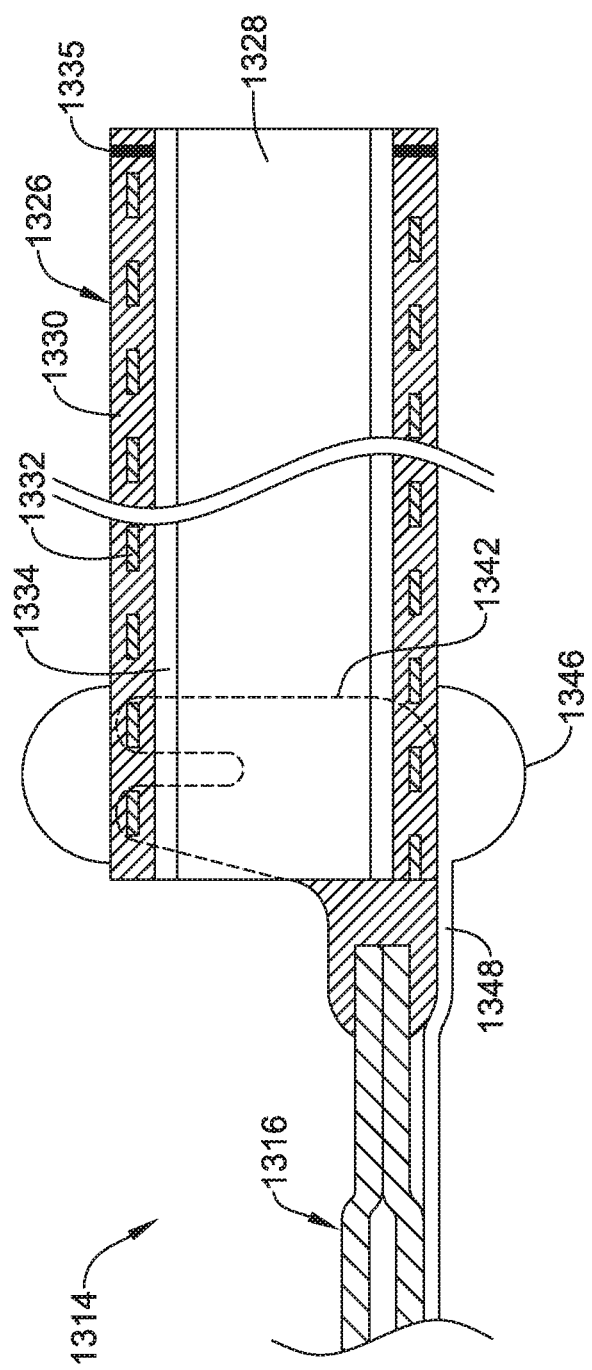

GUIDE EXTENSION CATHETER WITH EXPANDABLE BALLOON

CROSS-REFERENCE TO RELATED APPLICATIONS

This application claims priority under 35 U.S.C. § 119(e) to U.S. Provisional Application No. 62/303,213, filed Mar. 3, 2016, the entire disclosure of which is herein incorporated by reference.

TECHNICAL FIELD

The present disclosure pertains to medical devices and methods for manufacturing the same. More particularly, the present disclosure pertains to elongated intracorporeal medical devices including a guide extension catheter having an expandable balloon.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. There is an ongoing need to provide alternative medical devices as well as alternative methods for manufacturing and using medical devices.

BRIEF SUMMARY

This disclosure provides design, material, manufacturing method, and use alternatives for medical devices. An example guide extension catheter is disclosed. The guide extension catheter comprises:
 a proximal shaft having a first outer diameter;
 a distal sheath attached to the proximal shaft and having a second outer diameter greater than the first outer diameter;
 wherein the distal sheath is designed to extend past a coronary ostium and into a coronary artery so that another medical device can pass therethrough toward the coronary artery; and
 an expandable balloon coupled to the distal sheath.

Alternatively or additionally to any of the embodiments above, the expandable balloon is disposed along an outer surface of the distal sheath.

Alternatively or additionally to any of the embodiments above, the expandable balloon is disposed along an inner surface of the distal sheath.

Alternatively or additionally to any of the embodiments above, further comprising an inflation tube in fluid communication with the expandable balloon.

Alternatively or additionally to any of the embodiments above, an inflation lumen is defined through a wall of the distal sheath.

Alternatively or additionally to any of the embodiments above, an inflation lumen is defined through the proximal shaft.

Alternatively or additionally to any of the embodiments above, the distal sheath includes a skived distal tip.

Alternatively or additionally to any of the embodiments above, further comprising a distal guide tube positioned within the distal sheath and extending to a position adjacent to a distal end of the distal sheath.

An example method for accessing an intravascular target region is disclosed. The method comprises:
 positioning a guide catheter in a blood vessel adjacent to an ostium of a coronary artery;
 advancing a guide extension catheter through the guide catheter such that a distal end of the guide extension catheter extends distally beyond a distal end of the guide catheter and into the coronary artery, the guide extension catheter comprising:
  a proximal shaft having a first outer diameter,
  a distal sheath attached to the proximal shaft and having a second outer diameter greater than the first outer diameter, and
  an expandable balloon coupled to the distal sheath; and
 expanding the expandable balloon.

Alternatively or additionally to any of the embodiments above, further comprising advancing a treatment device through the distal sheath.

Alternatively or additionally to any of the embodiments above, the expandable balloon is an occlusion balloon, and wherein expanding the expandable balloon includes expanding the expandable balloon against an inner surface of the guide catheter; expanding the expandable balloon against one or more of the blood vessel, the ostium, or the coronary artery; or both to substantially prevent blood flow therethrough.

Alternatively or additionally to any of the embodiments above, the expandable balloon is an anchoring balloon, and further comprising anchoring a medical device within the distal sheath with the anchoring balloon.

Alternatively or additionally to any of the embodiments above, further comprising an inflation tube in fluid communication with the expandable balloon, and wherein inflating the expandable balloon includes passing inflation media through the inflation tube.

Alternatively or additionally to any of the embodiments above, an inflation lumen is defined through a wall of the distal sheath, and wherein inflating the expandable balloon includes passing inflation media through the inflation lumen.

Alternatively or additionally to any of the embodiments above, an inflation lumen is defined through the proximal shaft, and wherein inflating the expandable balloon includes passing inflation media through the inflation lumen.

Alternatively or additionally to any of the embodiments above, the distal sheath includes a skived distal tip.

Alternatively or additionally to any of the embodiments above, further comprising a distal guide tube positioned within the distal sheath and extending to a position adjacent to a distal end of the distal sheath.

An example guide extension catheter is disclosed. The guide extension catheter, comprises:
 a proximal shaft having a first outer diameter;
 a distal sheath attached to the proximal shaft and having a second outer diameter greater than the first outer diameter;
 wherein the distal sheath is designed to be positioned within a guide catheter such that a distal end of the distal sheath extends distally beyond a distal end of the guide catheter into an ostium of a coronary artery to anchor the guide catheter relative to the ostium so that another medical device can pass through the distal sheath toward a target region within the coronary artery;
 an expandable balloon coupled to the distal sheath; and
 wherein an inflation lumen is defined adjacent to the distal sheath, the inflation lumen being in fluid communication with the expandable balloon.

Alternatively or additionally to any of the embodiments above, the expandable balloon is an occlusion balloon disposed along an outer surface of the distal sheath.

Alternatively or additionally to any of the embodiments above, the expandable balloon is an anchoring balloon disposed along an inner surface of the distal sheath.

Alternatively or additionally to any of the embodiments above, at least a portion of the inflation lumen extends through a wall of the distal sheath.

Alternatively or additionally to any of the embodiments above, at least a portion of the inflation lumen extends through the proximal shaft.

Alternatively or additionally to any of the embodiments above, the distal sheath includes a skived distal tip.

Alternatively or additionally to any of the embodiments above, further comprising a distal guide tube positioned within the distal sheath and extending to a position adjacent to a distal end of the distal sheath.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 1 is a plan view illustrating an example guide catheter advanced through the aorta to the ostium of a coronary artery;

FIG. 2 is a plan view illustrating an example guide extension catheter used in conjunction with a guide catheter;

FIG. 3 is a partial cross-sectional side view of an example guide extension catheter;

FIG. 3A is a side view of a portion of an example guide extension catheter;

FIG. 16 is a partial cross-sectional side view of an example guide extension catheter.

Figure 4:
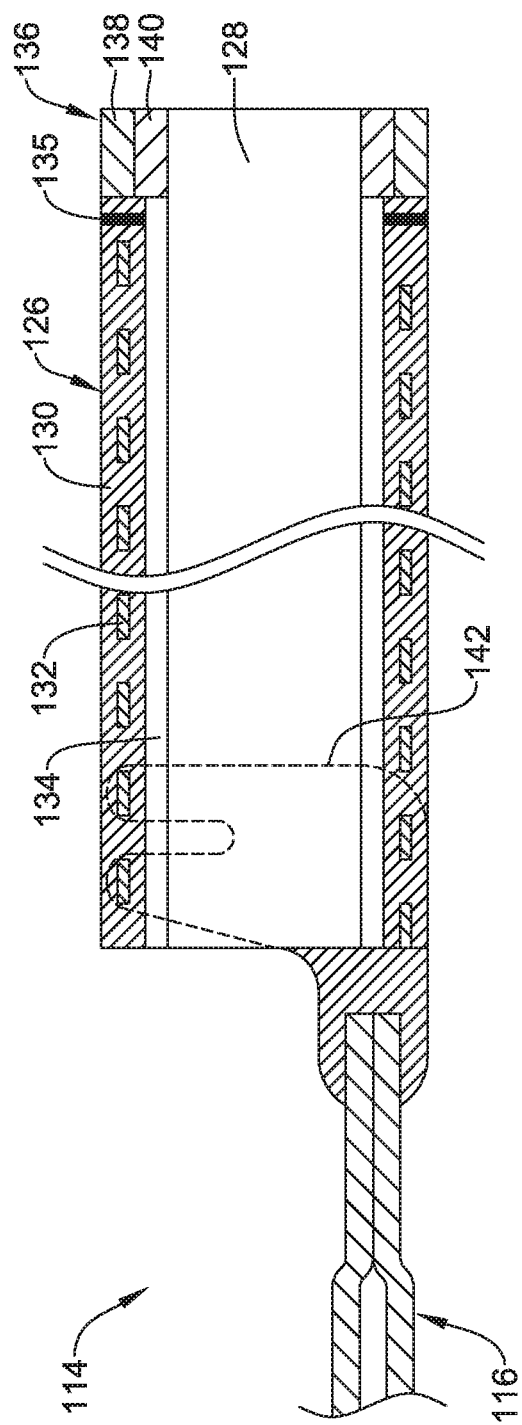
FIG. 4 is a partial cross-sectional side view of an example guide extension catheter.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Minimally-invasive cardiac interventions, such as percutaneous transluminal coronary angioplasty, are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1. When so positioned, a treatment catheter (e.g., balloon catheter, stent delivery system, etc.) may be advanced through the guide catheter 10 and into the coronary artery CA to a target location where the treatment catheter may be used to perform the appropriate cardiac intervention.

In order for the treatment catheter to efficiently reach the intended target location, maintaining the position of the guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. Thus, a distal end 12 of the guide catheter 10 may be shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Disclosed herein are medical devices and methods for making and using medical devices that may improve access to the coronary arteries CA. For example, FIG. 2 illustrates a guide extension catheter 14 extending through the guide catheter 10 and beyond the distal end 12 of the guide catheter 10 into the coronary artery CA. Because, for example, the guide extension catheter 14 may extend beyond the distal end 12 of the guide catheter 10, the guide extension catheter 14 may extend beyond the ostium O of the coronary artery CA and into a portion of the coronary artery CA. By extending beyond the ostium O, the guide extension catheter 14 may stabilize the positioning of the guide catheter 10 and allow for improved access to the coronary artery CA for a number of cardiac interventions.

FIG. 3 is a cross-sectional side view of the guide extension catheter 14. Here it can be seen that the guide extension catheter 14 may include a proximal shaft 16. The proximal shaft 16 may include a proximal portion 18 and a distal or ribbon portion 20. The proximal portion 18 may have a lumen 22 defined therein. In some embodiments, the lumen 22 extends along the entire length of the proximal portion 18. In other embodiments, the lumen 22 extends along only a portion of the length of the proximal portion 18. In addition, the proximal portion 18 may include both proximal and distal openings (e.g., positioned at the proximal and distal end of the proximal portion 18) such that the lumen 22 is open on both ends. Alternatively, one or both of the ends of the proximal portion 18 may be closed or otherwise sealed. For example, the distal end of the proximal portion 18 may be closed. In some embodiments, the proximal portion 18 may have an opening or port (not shown) formed in the wall of the proximal portion 18 and spaced from the proximal and/or distal end of the proximal portion 18. The port may or may not be in fluid communication with the lumen 22. A hub 24 may be attached to the proximal portion 18.

A distal sheath 26 may be attached to the proximal shaft 16. The distal sheath 26 may have a lumen 28 formed therein. In general, the lumen 28 (and/or the inner diameter of the distal sheath 26) may be larger than the lumen 22 (and/or the inner diameter of the proximal portion 18) and may be larger than the outer diameter of the proximal shaft 16. Accordingly, the lumen 28 may be sufficiently large so as to allow a therapeutic catheter (e.g., balloon catheter, stent delivery system, etc.) to pass there through. For example, when the guide extension catheter 14 is positioned within the guide catheter 10, the therapeutic catheter may extend within the guide catheter 10 alongside the proximal shaft 16 and through the lumen 28 of the distal sheath 26.

The distal sheath 26 may include a body portion 30. In some embodiments, the body portion 30 is made from one or more polymers such as those disclosed herein. This may include the use of polymers with a differing durometer along the length of the body portion 30. For example, a more proximal section of the body portion 30 may include a polymer or a polymer blend with a higher durometer and a more distal section of the body portion 30 may include a polymer or a polymer blend with a lower durometer. Portions of all of the length of the body portion 30 may be loaded with or otherwise include a radiopaque material.

In some instances, one or more radiopaque markers 35 may be disposed along the body portion 30. For example, a radiopaque marker 35 may be positioned adjacent to a distal end of the distal sheath 26. In some of these embodiments, a radiopaque marker may be positioned adjacent to a proximal end of the distal sheath 26. The distal sheath 26 may also include additional radiopaque markers positioned at suitable locations along its length. The shape, form, arrangement, and/or configuration of the radiopaque marker(s) 35 may also vary. For example, in some instances, the radiopaque marker 35 may be embedded in the body portion 30. In addition, the radiopaque marker may have a length in the axial direction that is greater than a length or thickness in the radial direction. Other shapes and/or configurations are contemplated.

The body portion 30 may also include a reinforcing member 32. The form of the reinforcing member 32 may vary. For example, the reinforcing member 32 may include a braid, coil, mesh, or the like made of a suitable material, such as a metal, a polymer, or the like.

An inner liner or layer 34 may be disposed along an inner surface of the body portion 30. The form of the inner liner 34 may vary. For example, the inner liner 34 may be a lubricious liner or otherwise include a lubricious material such as polytetrafluoroethylene.

The distal sheath 26 may be attached to a ribbon portion 20 of the proximal shaft 16. The arrangement and/or configuration of the attachment between the ribbon portion 20 and the distal sheath 26 may vary. For example, the distal sheath 26 may have an opening or lumen formed in a tube wall thereof and the ribbon portion 20 may be disposed within the opening. This may include necking, skiving, or pinching down the ribbon portion 20 and inserting the necked down portion into the opening. In some embodiments, inserting the ribbon portion 20 into the opening may secure the proximal shaft 16 to the distal sheath 26 via a mechanical bond. In some of these and in other embodiments, additional and/or alternative bonding may be utilized including those bonding mechanisms commonly used for medical devices (e.g., adhesive bonding, welding, thermal bonding, brazing, etc.).

Other attachment mechanisms are also contemplated for attaching the proximal shaft 16 to the distal sheath 26 including direct bonding (e.g., adhesive bonding, thermal bonding, welding, brazing, etc.), bonding that is facilitated by a third component such as a metal or polymer collar 42 that may be bonded between the ribbon portion 20 and the distal sheath 26. The collar 42 illustrated in FIG. 3 (and in other figures) is meant to be schematic in nature and is not intended to limit the collar to any particular shape or configuration. A number of different collars are contemplated for securing the proximal shaft 16 and the distal sheath 26. For example, FIG. 3A illustrates a collar 42a, which may be utilized with any of the guide extension catheters disclosed herein. For the purposes of this disclosure, any of the guide extension catheters disclosed herein may be considered to have a collar resembling the collar 42, a collar resembling the collar 42a, or another suitable collar. The collar 42a may include a base 54a. A cutout 56a may be formed in the base 54a. In at least some instances, the ribbon portion 20 may be disposed within the cutout 56a and attached to the collar 42a using a suitable bonding technique (e.g., welding). The collar 42a may also include a plurality of arms or struts 58a that are oriented at an angle and/or otherwise take a helical configuration. In addition, the material used for the collar 42 and/or the collar 42a may vary. For example, in some instances, the collar 42 and/or the collar 42a may be made from a radiopaque material, such as Pt—Ir. This may allow the distal sheath 26 to not have a separate radiopaque marker adjacent to the proximal end of the distal sheath 26, if desired.

The guide extension catheter 14 may also include a number of coatings that may, for example, reduce friction. For example, the proximal shaft 16 may have an inner and/or outer coating that includes a hydrophilic polymer that may reduce friction during tracking. An example coating may include BAYER CL-100, BIOSLIDE, NG-HPC, SLIP COAT, MDX, or the like. Other coating materials are contemplated including those disclosed herein.

FIG. 4 illustrates another example guide extension catheter 114 that may be similar in form and function to other guide extension catheters disclosed herein. The guide extension catheter 114 may include a proximal shaft 116 and a distal sheath 126. A collar 142 may be used to secure the proximal shaft 116 to the distal sheath 126. The distal sheath 126 may include a lumen 128, a body portion 130, a reinforcing member 132, a liner 134, and a radiopaque marker 135. The distal sheath 126 may also include a tip member 136. The tip member 136 may be considered to be a soft and/or an atraumatic tip. In some embodiments, the tip member 136 may be a single layer of material. Alternatively, the tip member 136 may include an outer layer 138 and an inner layer 140. The outer layer 138 and the inner layer 140 may be formed from the same material or from different materials. In some instances, the outer layer 138 and the inner layer 140 may include the same polymeric material and each may be loaded with the same or different radiopaque materials. For example, the inner layer 140 may include a polyether block amide loaded with approximately 75-95% (e.g., about 90%) by weight tungsten and outer layer 138 may include a polyether block amide loaded with approximately 30-50% (e.g., 40%) by weight bismuth subcarbonate. These are just examples. In other embodiments, the outer layer 138 and the inner layer 140 may be made from different materials.

Figure 5:
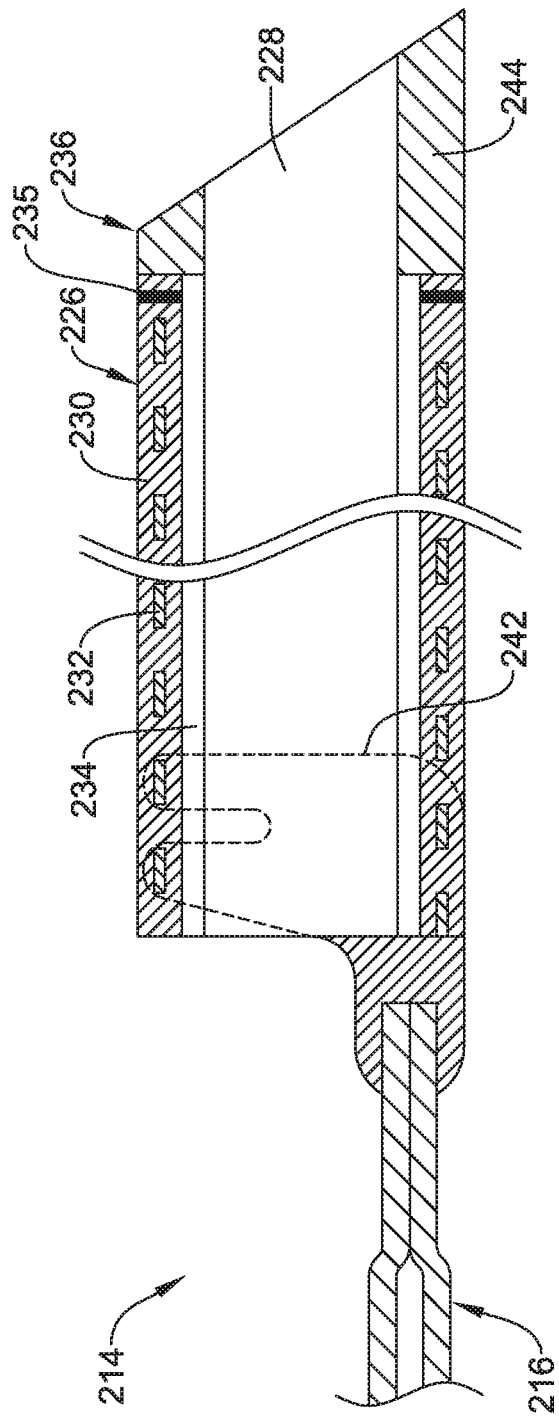
FIG. 5 is a partial cross-sectional side view of an example guide extension catheter.

FIG. 5 illustrates another example guide extension catheter 214 that may be similar in form and function to other guide extension catheters disclosed herein. The guide extension catheter 214 may include a proximal shaft 216 and a distal sheath 226. A collar 242 may be used to secure the proximal shaft 216 to the distal sheath 226. The distal sheath 226 may include a lumen 228, a body portion 230, a reinforcing member 232, a liner 234, and a radiopaque marker 235. The distal sheath 226 may also include a tip member 236. In some instances, the tip member 236 may have a tip body 244 with a skived end. The skived end may help to facilitate delivery of the guide extension catheter 314 (and/or a device passing therethrough). In addition, the skived end may also be softer and atraumatic.

Figure 6:
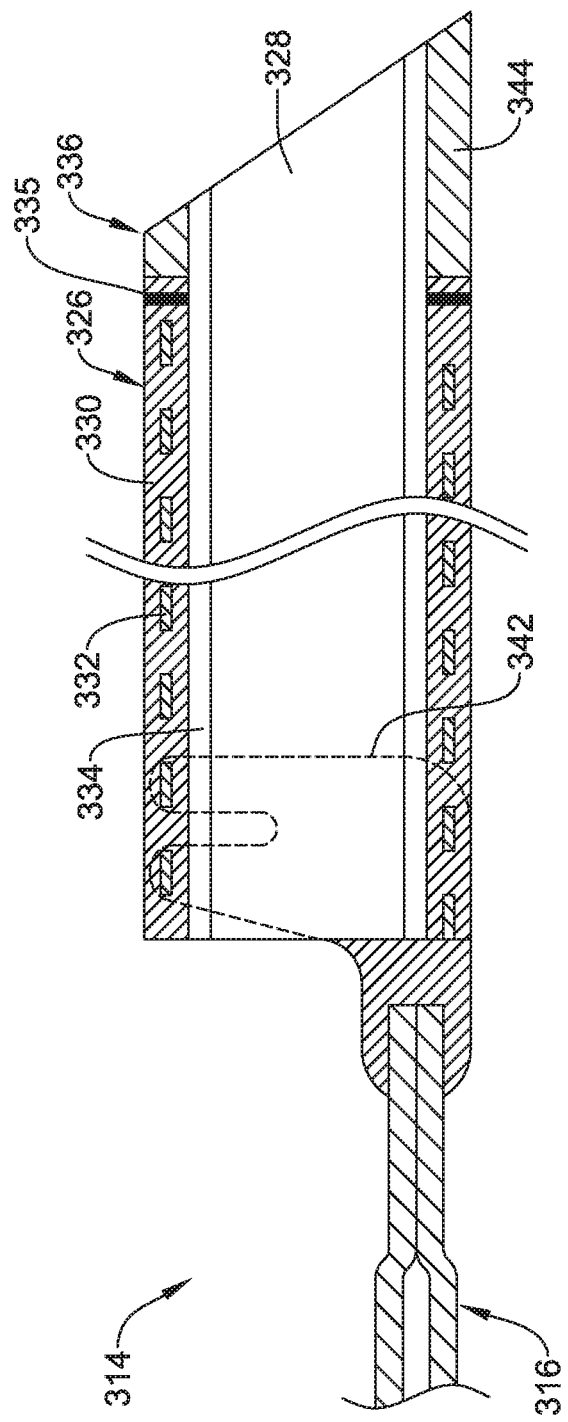
FIG. 6 is a partial cross-sectional side view of an example guide extension catheter.

FIG. 6 illustrates another example guide extension catheter 314 that may be similar in form and function to other guide extension catheters disclosed herein. The guide extension catheter 314 may include a proximal shaft 316 and a distal sheath 326. A collar 342 may be used to secure the proximal shaft 316 to the distal sheath 326. The distal sheath 326 may include a lumen 328, a body portion 330, a reinforcing member 332, a liner 334, and a radiopaque marker 335. The distal sheath 326 may also include a tip member 336. In some instances, the tip member 336 may have a tip body 344 with a skived end. The liner 334 may extend along the tip body 344.

Figure 7:
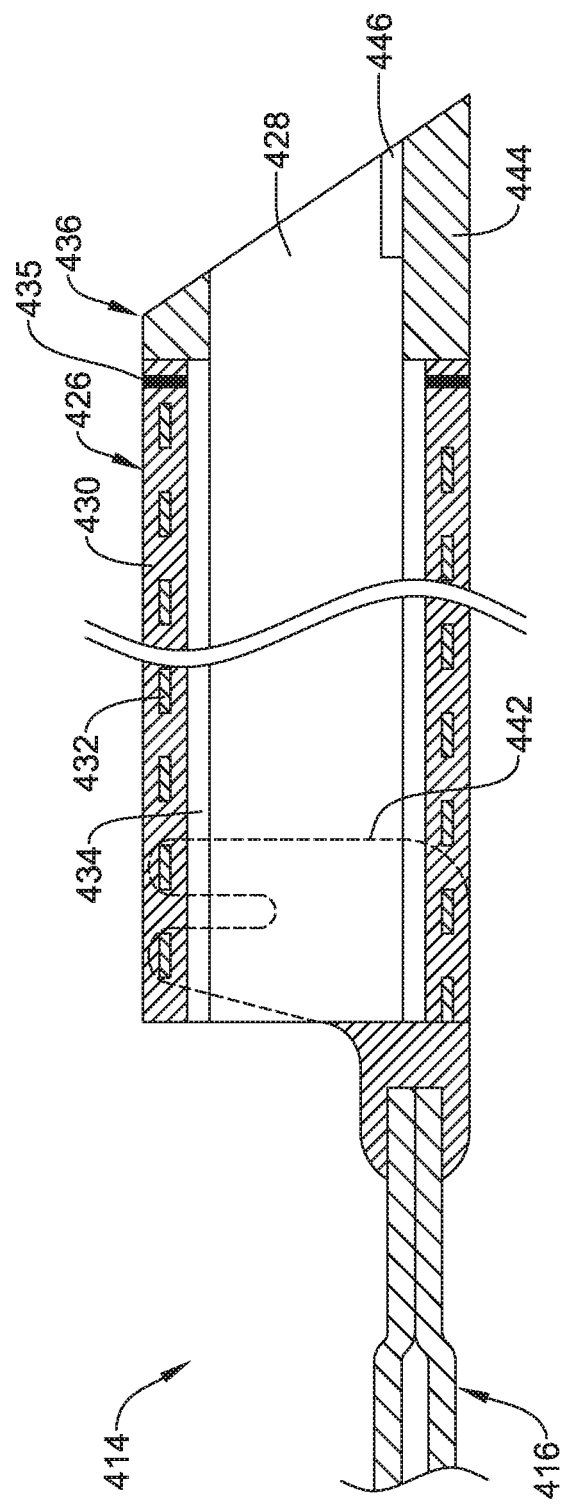
FIG. 7 is a partial cross-sectional side view of an example guide extension catheter.

FIG. 7 illustrates another example guide extension catheter 414 that may be similar in form and function to other guide extension catheters disclosed herein. The guide extension catheter 414 may include a proximal shaft 416 and a distal sheath 426. A collar 442 may be used to secure the proximal shaft 416 to the distal sheath 426. The distal sheath 426 may include a lumen 428, a body portion 430, a reinforcing member 432, a liner 434, and a radiopaque marker 435. The distal sheath 426 may also include a tip member 436. In some instances, the tip member 436 may have a tip body 444 with a skived end. A guidewire tube 446 may extend along at least a portion of the tip body 444. The guidewire tube 446 may be used as a conduit for a guidewire extending through the distal sheath 426.

In addition to the guidewire tube 446 or as an alternative to the guidewire tube 446, a magnet or magnetic material may be disposed adjacent to or embedded within the tip body 444. For example, a magnet may be disposed along the skived end of the tip body 444. In other instances, the tip body 444 (e.g., whether skived or not) may include a magnetic material embedded therein (e.g., powdered magnetic material). In other instances, the tip body 444 (e.g., whether skived or not) may include a magnetic material and/or a radiopaque material embedded therein (e.g., powdered magnetic material and/or radiopaque material). In other instances, the tip body 444 (e.g., whether skived or not) may include a magnetic material embedded therein and/or a radiopaque marker (e.g., powdered magnetic material and/or a radiopaque marker). The magnetic material may allow the guide extension catheter 414 to hold onto a guidewire, yet release when a device approaches along the guidewire. This may allow a clinician to leave a guidewire in place during an intervention rather than remove the guidewire in order to advance a device past the guidewire tube 446.

FIGS. 8-11 illustrate example guide extension catheters that include an expandable member or balloon along an outer surface of the distal sheath. Such a balloon may function as an occlusion balloon that is designed to block the flow of blood. The balloon may be designed to be expanded against tissue along a blood vessel, against tissue adjacent to the coronary ostium, against a coronary artery, against a guide catheter through which the guide extension member is disposed, or a combination thereof. Different inflation structures may be utilized to inflate the balloon as discussed herein. While an outer balloon may be considered to be an occlusion balloon, the balloon may also function in anchoring the guide extension catheter to tissue and or other devices. To the extent that it is appropriate, structures disclosed with respect to other guide extension catheters disclosed herein (e.g., soft tips, skived tips, the collar 42a, the guidewire tube 446, etc.) may be utilized with the guide extension catheters disclosed in FIGS. 8-11.

Figure 8:
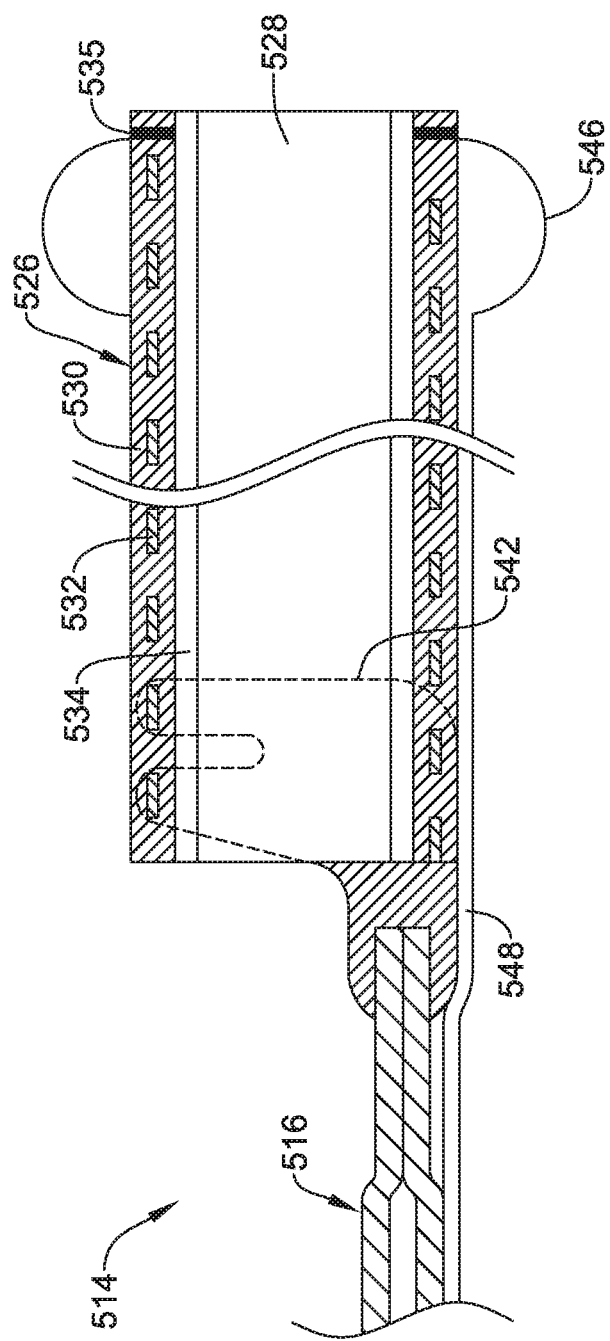
FIG. 8 is a partial cross-sectional side view of an example guide extension catheter.

FIG. 8 illustrates another example guide extension catheter 514 that may be similar in form and function to other guide extension catheters disclosed herein. The guide extension catheter 514 may include a proximal shaft 516 and a distal sheath 526. A collar 542 may be used to secure the proximal shaft 516 to the distal sheath 526. The distal sheath 526 may include a lumen 528, a body portion 530, a reinforcing member 532, a liner 534, and a radiopaque marker 535.

An expandable balloon 546 may be coupled to the distal sheath 526. As indicated above, the balloon 546 may function as an occlusion balloon. An inflation tube 548 may be in fluid communication with the balloon 546. The inflation tube 548 may extend along the outer surface of the distal sheath 526 and then further along the proximal shaft 516 to a position where an inflation device (e.g., a device for passing inflation media therethrough) may be connected.

Figure 9:
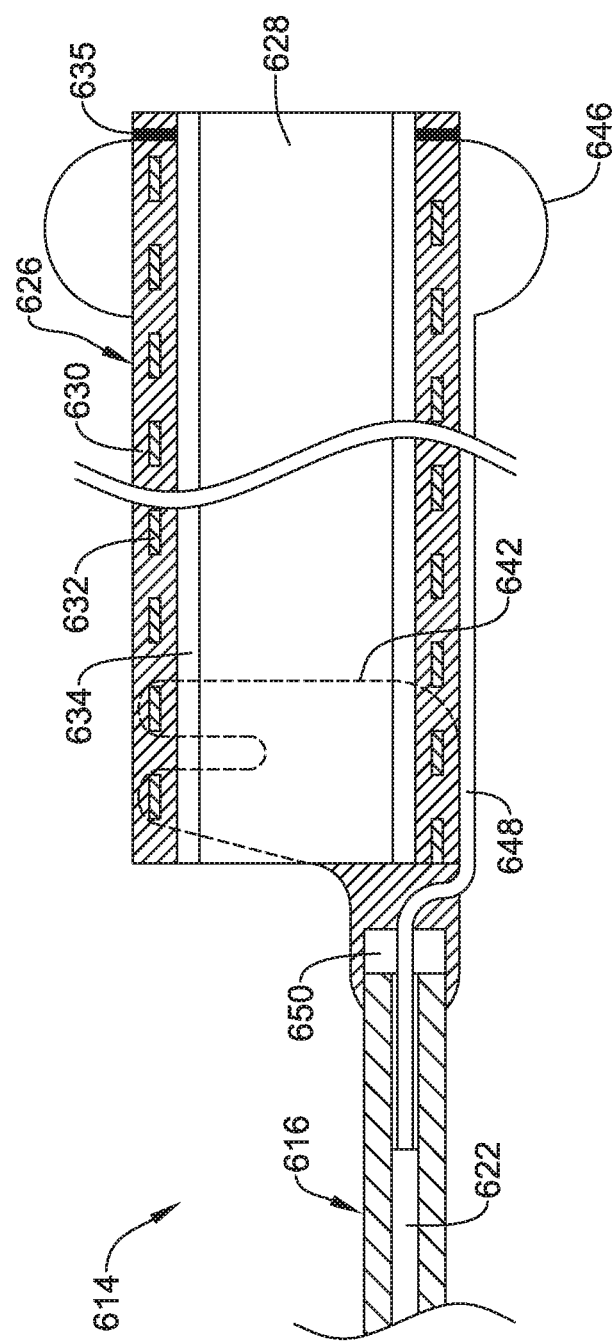
FIG. 9 is a partial cross-sectional side view of an example guide extension catheter.

FIG. 9 illustrates another example guide extension catheter 614 that may be similar in form and function to other guide extension catheters disclosed herein. The guide extension catheter 614 may include a proximal shaft 616 and a distal sheath 626. A collar 642 may be used to secure the proximal shaft 616 to the distal sheath 626. The distal sheath 626 may include a lumen 628, a body portion 630, a reinforcing member 632, a liner 634, and a radiopaque marker 635.

An expandable balloon 646 may be coupled to the distal sheath 626. An inflation tube 648 may be in fluid communication with the balloon 646. In some instances, the inflation tube 648 may be in fluid communication with the lumen 622 of the proximal shaft 616. A gap 650 may be positioned at the distal end of the proximal shaft 616. The gap 650 may help facilitate connection of the inflation tube 648 with the lumen 622 of the proximal shaft 616.

Figure 10:
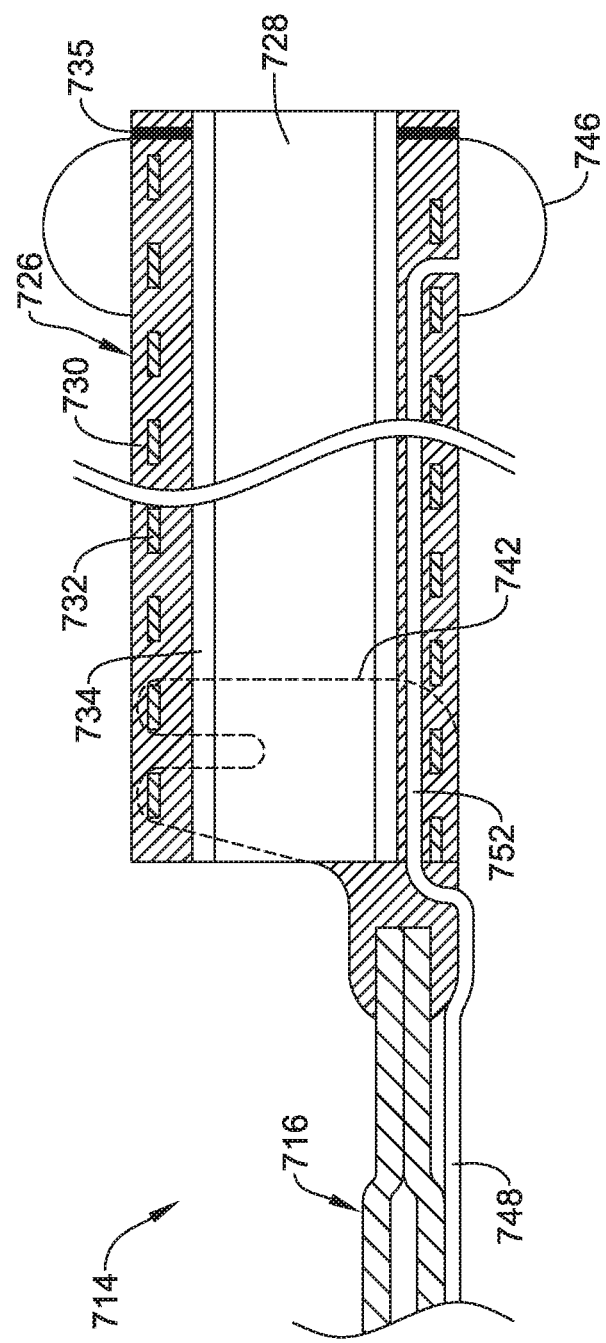
FIG. 10 is a partial cross-sectional side view of an example guide extension catheter.

FIG. 10 illustrates another example guide extension catheter 714 that may be similar in form and function to other guide extension catheter disclosed herein. The guide extension catheter 714 may include a proximal shaft 716 and a distal sheath 726. A collar 742 may be used to secure the proximal shaft 716 to the distal sheath 726. The distal sheath 726 may include a lumen 728, a body portion 730, a reinforcing member 732, a liner 734, and a radiopaque marker 735.

An expandable balloon 746 may be coupled to the distal sheath 726. An inflation tube 748 may be in fluid communication with the balloon 746. In some instances, the inflation tube 748 may be in fluid communication with an inflation lumen 752 formed in the distal sheath 726. In other words, the distal sheath 726 may have the inflation lumen 752 defined in the wall thereof and the inflation tube 748 may be connected to the inflation lumen 752. In some instances, the formation of the inflation lumen 752 may include the use of a mandrel placed along one or more of the layers of the distal sheath 726 during manufacturing of the distal sheath 726.

Figure 11:
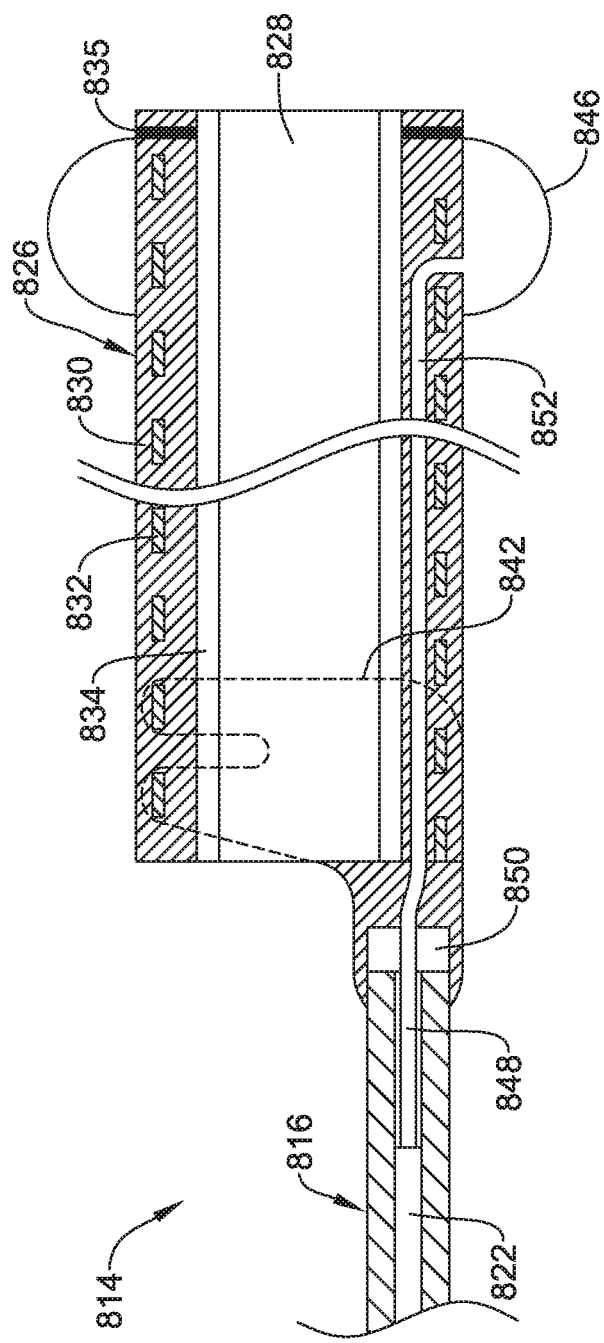
FIG. 11 is a partial cross-sectional side view of an example guide extension catheter.

FIG. 11 illustrates another example guide extension catheter 814 that may be similar in form and function to other guide extension catheters disclosed herein. The guide extension catheter 814 may include a proximal shaft 816 and a distal sheath 826. A collar 842 may be used to secure the proximal shaft 816 to the distal sheath 826. The distal sheath 826 may include a lumen 828, a body portion 830, a reinforcing member 832, a liner 834, and a radiopaque marker 835.

An expandable balloon 846 may be coupled to the distal sheath 826. An inflation tube 848 may be in fluid communication with the balloon 846. In some instances, the inflation tube 848 may be in fluid communication with the lumen 822 of the proximal shaft 816. A gap 850 may be positioned at the distal end of the proximal shaft 816. In some instances, the inflation tube 848 may also be in fluid communication with the inflation lumen 852 formed in the distal sheath 826.

FIGS. 12-15 illustrate example guide extension catheters that include an expandable member or balloon along an inner surface of the distal sheath. Such a balloon may function as an anchoring balloon that is designed to anchor another device (e.g., a guidewire, catheter, stent delivery system, or the like) within the distal sheath. Different inflation structures may be utilized to inflate the balloon as discussed herein. While an inner balloon may be considered to be an anchoring balloon, the balloon may also function in occluding flow of blood through the guide extension catheter. To the extent that it is appropriate, structures disclosed with respect to other guide extension catheters disclosed herein (e.g., soft tips, skived tips, the collar 42a, the guidewire tube 446, etc.) may be utilized with the guide extension catheters disclosed in FIGS. 12-15.

Figure 12:
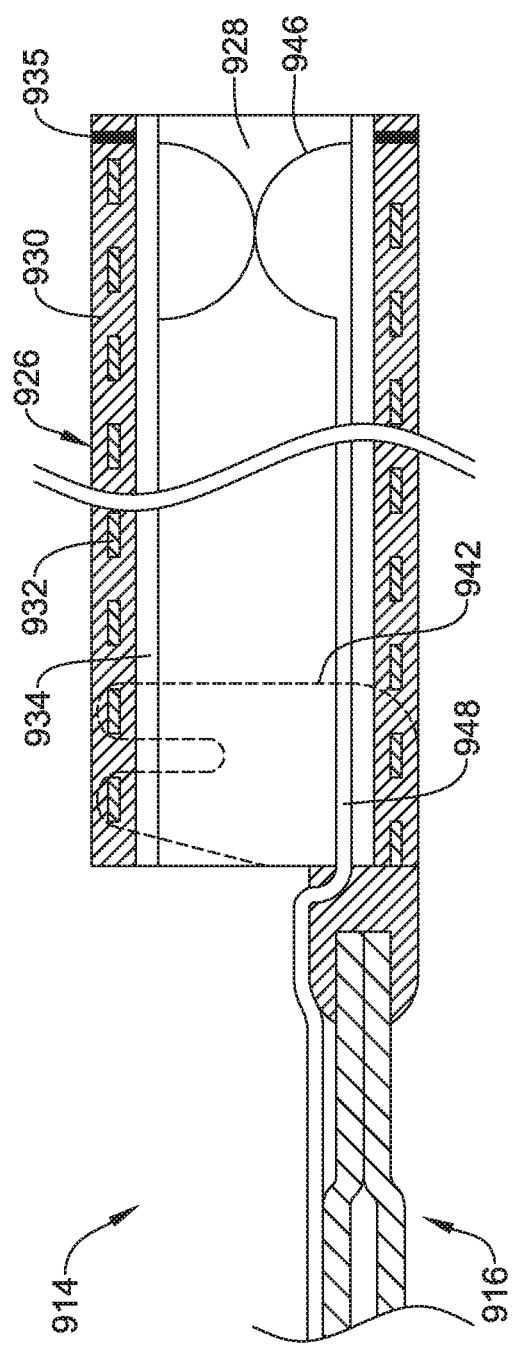
FIG. 12 is a partial cross-sectional side view of an example guide extension catheter.

FIG. 12 illustrates another example guide extension catheter 914 that may be similar in form and function to other guide extension catheters disclosed herein. The guide extension catheter 914 may include a proximal shaft 916 and a distal sheath 926. A collar 942 may be used to secure the proximal shaft 916 to the distal sheath 926. The distal sheath 926 may include a lumen 928, a body portion 930, a reinforcing member 932, a liner 934, and a radiopaque marker 935.

An expandable balloon 946 may be coupled to the distal sheath 926. An inflation tube 948 may be in fluid communication with the balloon 946. The inflation tube 948 may extend along an inner surface of the distal sheath 926 and then along the proximal shaft 916.

Figure 13:
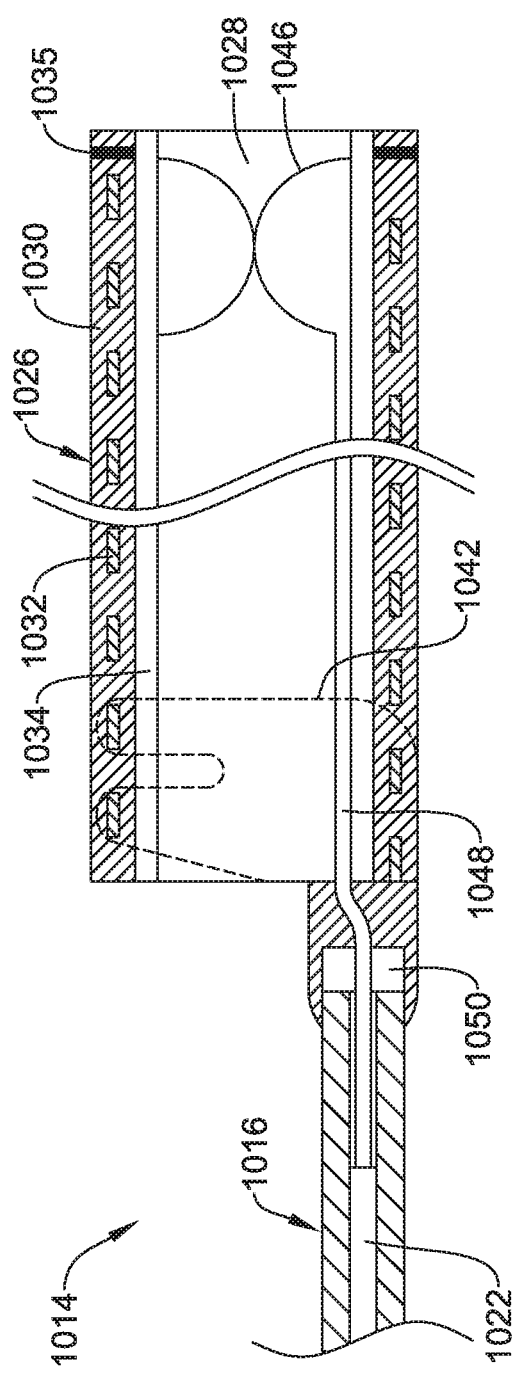
FIG. 13 is a partial cross-sectional side view of an example guide extension catheter.

FIG. 13 illustrates another example guide extension catheter 1014 that may be similar in form and function to other guide extension catheters disclosed herein. The guide extension catheter 1014 may include a proximal shaft 1016 and a distal sheath 1026. A collar 1042 may be used to secure the proximal shaft 1016 to the distal sheath 1026. The distal sheath 1026 may include a lumen 1028, a body portion 1030, a reinforcing member 1032, a liner 1034, and a radiopaque marker 1035.

An expandable balloon 1046 may be coupled to the distal sheath 1026. An inflation tube 1048 may be in fluid communication with the balloon 1046. In some instances, the inflation tube 1048 may be in fluid communication with the lumen 1022 of the proximal shaft 1016. A gap 1050 may be positioned at the distal end of the proximal shaft 1016.

Figure 14:
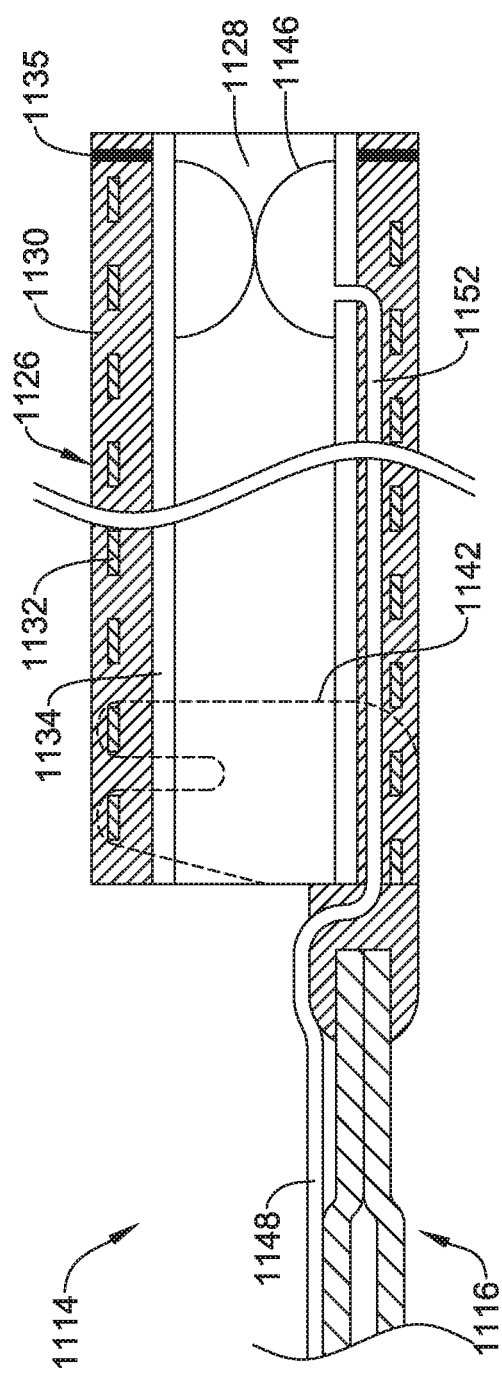
FIG. 14 is a partial cross-sectional side view of an example guide extension catheter.

FIG. 14 illustrates another example guide extension catheter 1114 that may be similar in form and function to other guide extension catheters disclosed herein. The guide extension catheter 1114 may include a proximal shaft 1116 and a distal sheath 1126. A collar 1142 may be used to secure the proximal shaft 1116 to the distal sheath 1126. The distal sheath 1126 may include a lumen 1128, a body portion 1130, a reinforcing member 1132, a liner 1134, and a radiopaque marker 1135.

An expandable balloon 1146 may be coupled to the distal sheath 1126. An inflation tube 1148 may be in fluid communication with the balloon 1146. In some instances, the inflation tube 1148 may be in fluid communication with an inflation lumen 1152 formed in the distal sheath 1126.

Figure 15:
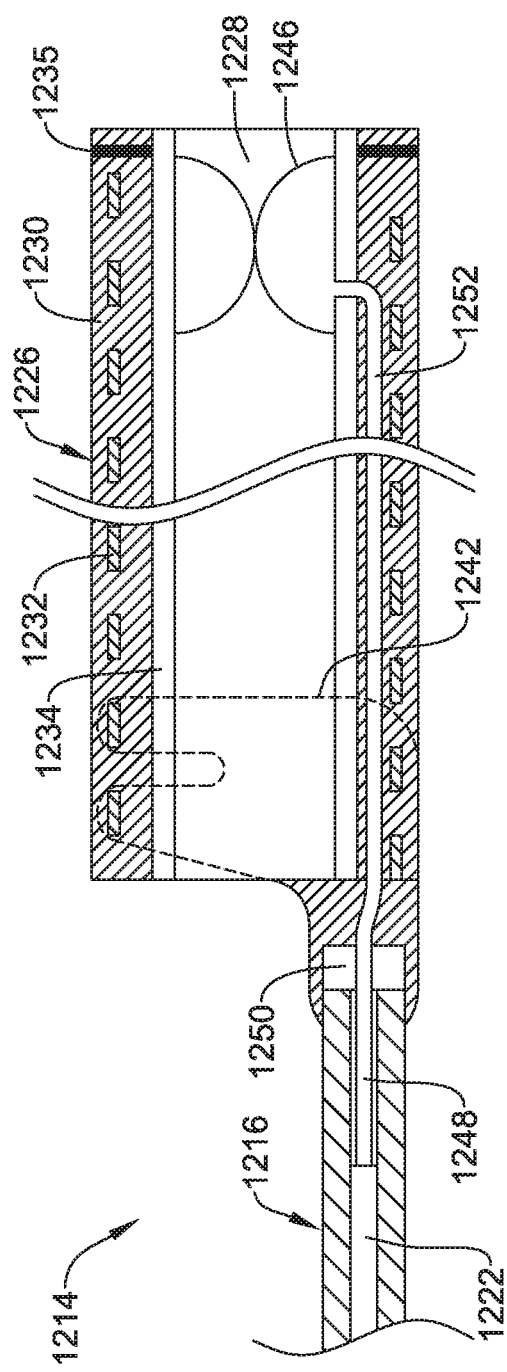
FIG. 15 is a partial cross-sectional side view of an example guide extension catheter.

FIG. 15 illustrates another example guide extension catheter 1214 that may be similar in form and function to other guide extension catheters disclosed herein. The guide extension catheter 1214 may include a proximal shaft 1216 and a distal sheath 1226. A collar 1242 may be used to secure the proximal shaft 1216 to the distal sheath 1226. The distal sheath 1226 may include a lumen 1228, a body portion 1230, a reinforcing member 1232, a liner 1234, and a radiopaque marker 1235.

An expandable balloon 1246 may be coupled to the distal sheath 1226. An inflation tube 1248 may be in fluid communication with the balloon 1246. In some instances, the inflation tube 1248 may be in fluid communication with the lumen 1222 of the proximal shaft 1216. A gap 1250 may be positioned at the distal end of the proximal shaft 1216. In some instances, the inflation tube 1248 may also be in fluid communication with the inflation lumen 1252 formed in the distal sheath 1226.

FIG. 16 illustrates another example guide extension catheter 1314 that may be similar in form and function to other guide extension catheters disclosed herein. The guide extension catheter 1314 may include a proximal shaft 1316 and a distal sheath 1326. A collar 1342 may be used to secure the proximal shaft 1316 to the distal sheath 1326. The distal sheath 1326 may include a lumen 1328, a body portion 1330, a reinforcing member 1332, a liner 1334, and a radiopaque marker 1335.

An expandable balloon 1346 may be coupled to the distal sheath 1326. An inflation tube 1348 may be in fluid communication with the balloon 1346. In this example, the expandable balloon 1346 is shown disposed along an outer surface of the distal sheath and positioned adjacent to a proximal end of the distal sheath 1326. This illustrates that the position of the balloon 1346 may vary. In addition, the inflation mechanism utilized to inflate the balloon 1346 may include structures similar to those disclosed herein (e.g., as shown in FIG. 8-11). The balloon 1346 may function to occlude and/or to anchor (e.g., anchor the guide extension catheter 1314 to, for example, a guide catheter).

The materials that can be used for the various components of the guide extension catheters disclosed herein and the various components thereof disclosed herein may include those commonly associated with medical devices. For simplicity purposes, the following discussion makes reference to the distal sheath 26 and other components of the guide extension catheter 14. However, this is not intended to limit the devices and methods described herein, as the discussion may be applied to other similar tubular members and/or components of tubular members or devices disclosed herein.

The distal sheath 26 and other components of the guide extension catheter 14 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer, CRISTAMID® available from Elf Atochem, VESTAMID®, or the like), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the guide extension catheter 14 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guide extension catheter 14 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guide extension catheter 14 to achieve the same result.

In some embodiments, a degree of Magnetic Resonance Imaging (MRI) compatibility is imparted into the guide extension catheter 14. For example, the guide extension catheter 14, or portions thereof, may be made of a material that does not substantially distort the image and create substantial artifacts (e.g., gaps in the image). Certain ferromagnetic materials, for example, may not be suitable because they may create artifacts in an MRI image. The guide extension catheter 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. Patent Application No. 62/169,541 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A guide extension catheter, comprising:
a proximal shaft having a first outer diameter;
a collar attached to the proximal shaft;
a distal sheath attached to the collar, the distal sheath having a second outer diameter greater than the first outer diameter;
wherein the distal sheath is designed to extend past a coronary ostium and into a coronary artery so that another medical device can pass therethrough toward the coronary artery; and
an annular expandable balloon coupled to the distal sheath, the expandable balloon being disposed along an inner surface of the distal sheath;
wherein the distal sheath includes an outer surface and wherein the outer surface is free of an outer expandable balloon;
wherein the expandable balloon is configured to fully occlude flow through the distal sheath and to anchor a device extending through the distal sheath.

2. The guide extension catheter of claim 1, further comprising an inflation tube in fluid communication with the expandable balloon.

3. The guide extension catheter of claim 1, wherein an inflation lumen is defined through a wall of the distal sheath.

4. The guide extension catheter of claim 1, wherein an inflation lumen is defined through the proximal shaft.

5. The guide extension catheter of claim 1, wherein the distal sheath includes a skived distal tip.

6. The guide extension catheter of claim 1, further comprising a distal guide tube positioned within the distal sheath and extending to a position adjacent to a distal end of the distal sheath.

7. A guide extension catheter, comprising:
a proximal shaft having a first outer diameter;
a distal sheath attached to the proximal shaft with a collar, the distal sheath having a second outer diameter greater than the first outer diameter;
wherein the distal sheath is designed to be positioned within a guide catheter such that a distal end of the distal sheath extends distally beyond a distal end of the guide catheter into an ostium of a coronary artery to anchor the guide catheter relative to the ostium so that another medical device can pass through the distal sheath toward a target region within the coronary artery;
an expandable balloon coupled to the distal sheath, the expandable balloon being ring-shaped and disposed along an inner surface of the distal sheath;
wherein the distal sheath includes an outer surface and wherein the outer surface is free of an outer expandable balloon;
wherein the expandable balloon is configured to fully occlude flow through the distal sheath and to anchor a medical device extending through the distal sheath; and
wherein an inflation lumen is defined adjacent to the distal sheath, the inflation lumen being in fluid communication with the expandable balloon.

* * * * *